(12) United States Patent
Joosten et al.

(10) Patent No.: US 8,765,413 B2
(45) Date of Patent: *Jul. 1, 2014

(54) CELL CULTIVATION PROCESS

(75) Inventors: Christoph E. Joosten, Basel (CH);
Christian Leist, Basel (CH); Jörg Schmidt, Basel (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/643,996

(22) PCT Filed: Apr. 25, 2011

(86) PCT No.: PCT/EP2011/056507
§ 371 (c)(1),
(2), (4) Date: Feb. 5, 2013

(87) PCT Pub. No.: WO2011/134919
PCT Pub. Date: Nov. 3, 2011

(65) Prior Publication Data
US 2013/0130316 A1    May 23, 2013

Related U.S. Application Data

(60) Provisional application No. 61/327,846, filed on Apr. 26, 2010.

(51) Int. Cl.
*A61K 38/00* (2006.01)
*C07K 16/00* (2006.01)
*C07K 14/005* (2006.01)
*C12N 15/81* (2006.01)

(52) U.S. Cl.
USPC ...... 435/69.6; 435/70.21; 435/70.3; 435/70.1

(58) Field of Classification Search
None
See application file for complete search history.

(56) References Cited

U.S. PATENT DOCUMENTS 5,672,502 A * 9/1997 Birch et al. .................. 435/383
2005/0019859 A1    1/2005 Burnett et al.

FOREIGN PATENT DOCUMENTS

EP    1757700 A2    2/2007
WO    2008141207 A1    11/2008

OTHER PUBLICATIONS

Oguchi et al "pH condition in temperature shift cultivation enhances cell longevity and specific Mab productivity in CHO culture" 2006 Cytotechnology 52, 199-207.*
Hyun et al. "Differences in optimal pH an Temperature for cell growth and antibody prodction between two chinese hamster ovary clones derived from the same parental clone" 2007 J. Microbiol. Biotechnol. 2007 17, 712-720.*
Borys et al "Culture pH affects expression rates and glycosylation of recombinant mouse placental lactogen proteins by chinese hamster ovary (CHO) cells" 1993 Biotechnology 11, 720-724.*
Evelyn Trummer, et al. "Process Parameter Shifting: Part II. Biphasic Cultivation—A Tool for Enhancing the Volumetric Productivity of Batch Processes Using Epo-Fc Expressing CHO Cells", Biotechnology and Bioengineering, vol. 94, No. 6, Aug. 20, 2006, pp. 1045-1052.
Sung Kwan Yoon, et al. "Biphasic culture strategy for enhancing volumetric erythropoietin productivity of Chinese hamster ovary cells" Enzyme and Microbial Technology 39 (2006) 362-365.
Gomez et al. Biotechnology Progress, vol. 26, No. 5, Sep. 2010, pp. 1438-1445, XP002638898.
Paul et al., "Maintaining Product Titer While Replacing Undefined Components in a CHO Culture System", Bioprocess International, 17(8):30-38, 2009.

* cited by examiner

*Primary Examiner* — Suzanne M Noakes
*Assistant Examiner* — Gerard Lacourciere
(74) *Attorney, Agent, or Firm* — Andrew Holmes

(57) ABSTRACT

This invention relates to a cell culture process for the production of polypeptides in mammalian CHO cells characterized by one or more temperature and pH shifts which are adjusted in respect to their timing and step size to reduce cell death, increase product yield and improve product quality.

18 Claims, 6 Drawing Sheets

○ Experiment 1 (with pH shift)
▨ Experiment 2 (without pH shift)
▨ Experiment 3 (without pH shift)

CELL CULTIVATION PROCESS

CROSS REFERENCE TO RELATED APPLICATIONS

This application is a U.S. National Phase patent application of PCT/EP2011/056507, filed Apr. 25, 2011, which claims priority to U.S. Provisional patent application Ser. No. 61/327,846, filed, Apr. 26, 2010, all of which are hereby incorporated by reference in the present disclosure in their entirety.

TECHNICAL FIELD OF THE INVENTION

This invention relates to the general field of biotechnology, particularly the cultivation of cells and their use for the production of polypeptides at industrial scale.

The present invention provides cell culture processes characterized by at least one temperature shift and at least one pH shift. These processes are suitable for the cultivation of cells with high cell viabilities, preferably mammalian cells like CHO cells. The cell culture processes according to the present invention further allow obtaining high polypeptide productivities when used for the production of a polypeptide, in particular by recombinant expression of polypeptides in mammalian cell culture systems, in particular at industrial scale.

TECHNICAL BACKGROUND OF THE INVENTION

The preparation of polypeptides using recombinant technology has developed into a standard procedure during the last couple of decades. The access to recombinant polypeptides by cloning the genes encoding the respective polypeptide followed by subsequent transformation of suitable expression hosts with the gene to be expressed and final production and purification of the obtained recombinant polypeptide product has provided access to a whole new class of biologically designed and produced therapeutics.

Pharmaceutically active compounds have been prepared in increasing numbers in the pharmaceutical industry using recombinant DNA technology followed by production processes developed in the field of bioengineering.

Such biological products include monoclonal antibodies, which have been developed into important treatment options in various medical fields including autoimmune diseases, inflammatory disorders, immunosuppression, oncology or the like.

Development of such therapeutics of biological origin requires production at industrial scale thereby providing access to large amounts of recombinant polypeptide. Preferred expression systems are mammalian cell cultures which are superior to most other eukaryotic systems based on insect cells, yeast or the like, or even traditional prokaryotic expression systems.

However, mammalian cell culture includes tremendous challenges especially at the industrial scale. Production facilities for mammalian cell culture require thorough optimization of many process conditions.

In particular, cell culture processes for the production of polypeptides in mammalian cells require continuous optimization of the culture conditions and their adaptation to specific cell lines or products in order to reach a high volumetric product yield in combination with optimal product quality.

Much previous effort has concentrated on the basic parameters of cell culture media including their composition concerning e.g., kinds and concentrations of ions, amino acids, vitamins or trace elements or the osmolality of the medium. Further important parameters, which have been in the focus of research, are e.g. feed composition or feeding schedules to reach optimal cell growth.

Also temperature and pH as basic physiological parameters are known to have significant influence on the culturing of mammalian cells. The temperature in general considerably affects the growth state and the viability of cells. In addition to this, it may, however, also more specifically influence the polypeptide product and its characteristics by altering e.g. the glycosylation (US 2003/0190710 A1; EP 1 373 547 A1; US 2004/0214289 A1).

The pH at which the growth medium and the cells are maintained can also influence and alter cell growth and polypeptide production in a specific manner that depends on the particular cell line and product (Sauer et al. Biotechnology and Bioengineering 2000, Vol 67, pg. 586-597: Yoon et al., Biotechnology and Bioengineering 2004, Vol 89, pg. 346-356; Kuwae et al., Journal of Bioscience and Bioengineering 2005 Vol 100, pg. 502-510).

Over the time course of culturing, the requirements of the cells may change. While in the beginning it is advantageous to optimize conditions towards improved cell growth, in later stages enhanced cell survival and maintenance of the viable cell density in connection with obtaining high product titers become important. In this respect introducing one or more temperature steps during cell culturing has been suggested (Chen et al., J Biosci Bioeng. 2004; 97 (4):239-43). For this, mammalian cells are cultured at least at two different temperatures, wherein the first higher temperature is optimized for cell growth while the second or third lower temperature is selected to improve the productivity of the cells (e.g. Weidemann et al., Cytotechnology. 1994, 15(1-3):111-6: WO 00/36092; EP 0 764 719 A2, US 2005/019859, EP 1 575 998, US 2008/081356). Other documents describe the use of temperature steps in combination with additional specific media features. EP 1 757 700 A2 e.g. discloses a temperature step in combination with the presence of butyrate salts as a media component, while EP 1 789 571 A1 describes a temperature step combined with a defined amino acid content.

Also other cell culture conditions have been changed. U.S. Pat. No. 5,856,179 has introduced a method for producing polypeptides in a fed batch cell culture, wherein during culturing the osmolality of the medium is considerably altered from around 280-330 mOsm in the major growth phase to about 400-600 mOsm during the production phase.

WO 02/101019 has looked at many specific media components such as glutamine and glucose concentrations, including changes in temperature and pH. However, it was found that a pH shift in high glucose media has a negative impact on the culture and that it is not recommended to reduce the pH during the growth or production phase.

WO 2008/026445 discloses a method for production of polypeptides wherein cell culture conditions are changed from one set of culture conditions to a second set and wherein this change is combined with specific media features concerning the content of specific amino acids. The change in conditions specifically relates to shifts in temperature. Other changes in conditions such as pH or osmolality are generally mentioned as additional options, however, particular parameter settings are not specified.

Considering the above challenges and existing disadvantages, there is a continued need in the field of industrial biotechnology for improved culture processes which allow producing recombinant polypeptides at an industrial scale with even higher yields, i.e. improved specific and overall productivity, and increased product quality.

A specific technical objective of polypeptide production processes is to maintain high cell viabilities and to maximize the final yield of polypeptide by optimizing the parameters of the overall cell cultivation process.

SUMMARY OF THE INVENTION

The present invention relates to combining temperature and pH shifts in a process for production of recombinant polypeptides. Adapted to the needs of recombinant cells, in particular CHO cells, specific combinations of these two parameters lead to increased productivity of the cells as well as improved product quality of the recombinantly produced polypeptides. In particular, the present invention has found positive effects based on the particular timing and scheduling of the temperature and pH shift(s) in absolute and relative terms as well as concerning the particular magnitude of the shifts.

According to one aspect of the invention, there is disclosed a process for the production of a recombinant polypeptide comprising culturing CHO cells in a medium and expressing the recombinant polypeptide wherein the temperature and the pH are changed during the process.

In particular, the process according to the present invention involves at least one temperature shift and at least one pH shift. In one embodiment of the present invention, a shift from a first higher to a second lower temperature is carried out after the cells are first grown and maintained for at least 3 days, alternatively at least 4 days, or at least 5 days at a first temperature. The second lower temperature is about 1 to about 8° C. lower than the first temperature. In another alternative embodiment of the present invention, the temperature shift is e.g., between about 2 and about 5° C., in particular about 4° C. or about 3.5° C. The second temperature is then maintained for at least two days. The second temperature may be maintained until harvest.

According to one embodiment of the present invention, the first temperature preferably is in the range of between about 33° C. and about 38° C., and the second temperature preferably is in the range of between about 30° C. and about 37° C.

In addition to the shift in temperature also the pH is changed from a first to a second pH. Thus, the processes according to the present invention comprise at least one pH shift. In particular, the cells are grown at a first pH value for at least 2 days and the pH is then shifted to a second pH value which is between about 0.05 and about 1 pH units lower than the first pH and the cells are grown at said second pH for at least 1 day, alternatively for at least 2 days. In some embodiments, the second pH will be maintained until harvest.

The first pH value preferably is in the range of between about pH 6.8 and about pH 7.5. The second pH value preferably is in the range of between about pH 6.0 and about pH 7.1.

Thus, one embodiment of the present invention is a process for the production of a recombinant polypeptide comprising culturing CHO cells in a medium under conditions comprising at least one temperature shift and at least one pH shift and expressing the recombinant polypeptide
wherein
the cells are grown at a first temperature for at least 3 days and the temperature is then shifted to a second temperature which is between about 1 and about 8° C. lower than the first temperature and the cells are maintained at said second temperature for a period of at least another 2 days;

the cells are grown at a first pH value for at least 2 days and the pH is then shifted to a second pH value which is between about 0.05 and about 1 pH units lower than the first pH and the cells are grown at said second pH for at least 1 day.

The process according to the present invention can optionally comprise a second pH shift, which follows the first pH shift after at least 1 day. If the first pH shift is followed by a second pH shift after at least 1 day then the third pH value is about 0.05 pH units to about 1 pH unit higher than the second pH value. The third pH value may be maintained until harvest.

The cell culture process according to the present invention includes active and/or passive pH shifts, i.e. the pH is altered "actively" by a change in the setpoint of the pH to a new value and/or "passively" by allowing a change of the pH of the medium by accumulation of metabolic products, thus following a cell culture specific metabolic pH profile within a predefined pH range. In a preferred embodiment of the invention the active shift is induced by adding the respective pH changing and regulating agent(s) known to the skilled person, such as acids, for example HO, or bases, for example NaOH. In a further preferred embodiment of the process, this is accomplished by defining one pH setpoint and a deadband wherein the pH is allowed to change. In contrast to the active shift, the passive shift or change in pH is not induced by adding the respective pH changing agent(s).

In a further aspect, the process according to the invention is carried out using a medium that is protein- and serum-free. Preferably, the medium is characterized by a total amino acid content of between about 40 mM and about 100 mM, alternatively between about 50 and about 100 mM.

A preferred process as defined above is done in fed batch mode comprising feeding of at least two nutrient solutions that are added to the culture. In such a process, e.g. one of the feed solutions added to the culture medium is a feed comprising the dipeptide cystine and the amino acid tyrosine. It is further preferred that the feed comprises the dipeptide cystine and the amino acid tyrosine at respective concentrations in the range of about 6.5 g/l and about 8.0 g/l and in the range of about 9 g/l and about 11 g/l in an aqueous solution at a basic pH of above 10. In particular, concentrations may be about 7.25 g/l for cystine and about 10.06 g/l for tyrosine. In a preferred embodiment, the feed solution comprising cystine and tyrosine is added to the culture medium in the range of about 0.2 and about 0.8 wt % of the initial culture medium weight per day or alternatively at about 0.4 wt % of the initial cell culture medium weight per day.

The process according to the invention is preferably used for the production of a recombinant polypeptide that is glycosylated. According to specific embodiments, the polypeptide is an antibody or antibody fragment.

BRIEF DESCRIPTION OF THE DRAWINGS

The invention will be better understood by reference to the following examples and figures. The examples, however, are not intended to limit the scope of the invention.

DETAILED DESCRIPTION OF THE INVENTION

Figure 1:
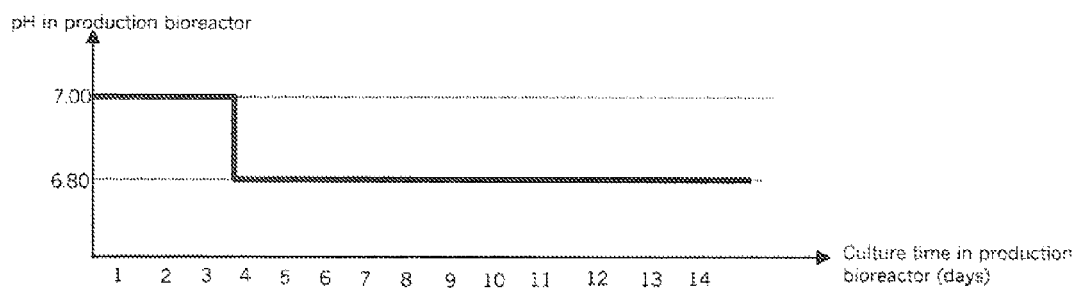
FIG. 1 is an illustration of the step-change implementation of an active pH shift with a shift from pH 7.00 to 6.80.

According to the present invention, a process for the preparation of a recombinant polypeptide comprises culturing CHO cells and expressing the recombinant polypeptide wherein the temperature and the pH are changed during the process. The present invention seeks to improve the process of large scale production of polypeptides in CHO cell culture by dynamically adapting cell culture conditions over the time course of culturing including temperature and pH shifts.

The term "large-scale production" of polypeptides relates to the amounts typically required for the industrial production of recombinant polypeptides used for preparation of therapeutically active biopharmaceuticals. Cell cultures with cell culture media of at least 500 L volume, or at least 1000 L, or alternatively at least 5000 L or even higher volumes typically represent large-scale production applications.

The term "cell culture medium" as used herein refers to an aqueous solution of nutrients which can be used for growing cells over a prolonged period of time. Typically, cell culture media include the following components: A source of energy, which will be usually a carbohydrate compound, preferably glucose, amino acids, preferably the basic set of amino acids, including all essential amino acids, vitamins and/or other organic compounds which are required at low concentrations, free fatty acids, and inorganic compounds including trace elements, inorganic salts, buffering compounds and nucleosides and bases.

The use of cell culture media in the field of pharmaceutical industry, for instance for the production of therapeutically active recombinant polypeptides, does generally not allow the use of any material of biological origin due to safety and contamination issues. Therefore, the cell culture medium according to the present invention is preferably a serum- and/or protein-free medium. The term "serum- and/or protein-free medium" represents a fully chemically defined medium, containing no additives from animal source like tissue hydrolysates, e.g. fetal bovine serum or the like. Further, proteins, especially growth factors like insulin, transferrin or the like are also preferably not added to the cell culture according to the present invention. Preferably, the cell culture medium according to the present invention is also not supplemented with a hydrolysed protein source like soybean, wheat or rice peptone or yeast hydrolysate or the like.

The term "temperature shift" as used herein refers to a change in the temperature of the culture in a bioreactor/culture vessel by actively altering the setpoint of the temperature to a lower value. The temperature is first controlled and stabilized at a defined temperature for a period of time and after changing the setpoint is then stabilized at another defined temperature for a period of time. The temperature step does not refer to small spontaneous temperature fluctuations in the culture.

The term "pH shift" as used herein refers to a change in the pH of the culture in a bioreactor/culture vessel by actively altering the setpoint of the pH to a lower or higher value or by allowing a pH shift to occur between an upper and lower pH limit.

Depending on the size of the culture vessel/bioreactor and the culture volume, the shift in the respective parameter as measured in the medium may take from a few minutes to several hours.

The pH can be shifted in two different ways, by an active and/or passive approach as described in more detail below.

The term "active shift" in the pH is defined by a change in the setpoint of the pH to a new value. In a preferred embodiment of the invention the active shift is induced by adding the respective pH changing and regulating agent(s) known to the skilled man.

The term "passive shift" indicates that during a passive shift in pH the cells themselves are allowed to change the pH of the medium by accumulation of metabolic products, thus following a cell culture specific metabolic pH profile within a predefined pH range. In one embodiment of the process this is accomplished by defining one pH setpoint and a deadband wherein the pH is allowed to change. In contrast to the active shift, the passive shift or change in pH is not induced by adding the respective pH changing agent(s).

pH regulating agents are added to the cultures in order to maintain the pH at a specific setpoint or to change the pH during a pH shift. Typical pH regulating agents used for cell culturing purposes include liquid base or acid solutions such as NaOH or HCl. Those pH regulating agents are added to the media in the culture vessel/bioreactor. Alternatively, the cell culture medium can be gassed with $CO_2$ to adjust the pH.

According to a first aspect of the invention, there is disclosed a process for the preparation of a recombinant polypeptide comprising culturing CHO cells and expressing the recombinant polypeptide wherein the temperature and the pH are changed during the process. More in particular, a shift from a first higher to a second lower temperature occurs after the cells are first grown and maintained for at least three days, alternatively at least 4 days, or at least 5 days at a first temperature. This second lower temperature is about 1 to about 8° C. lower than the first temperature. In another embodiment of the invention, the temperature shift may be between about 2 and about 5° C., in some implementations it is about 4° C. or about 3.5° C. This second temperature is then maintained for at least two days. In addition to the shift in temperature also the pH is changed from a first to a second pH.

The exact parameters concerning the shift in temperature and the pH are determined beforehand and adapted based on the needs of the cell line which has been transfected with one or more particular gene constructs coding for the respective polypeptide that is produced. Alternatively the needs can be made dependant on metabolic parameters that are determined during culturing for large scale production in a bioreactor.

A temperature shift from a higher temperature to a lower temperature is useful because the first temperature is optimal for cell growth while the lower temperature reduces the rate of cell death. A reduced temperature will therefore allow for a longer maintenance of the high viable cell density. The cell-specific productivity of the polypeptide of interest at this reduced temperature is usually not drastically reduced relative to the initial temperature, sometimes cell-specific productivity can be the same or sometimes even superior. A longer maintenance of high viable cell density can in addition provide the advantage of minimizing the formation of product of inadequate quality. The combination of these factors enables a high volumetric productivity and the achievement of high titers of product of interest of adequate quality at the time of harvest. In one embodiment the first temperature is in the range of between about 33° C. and about 38° C. In another example the first temperature is between about 36° C. to about 38° C. The second temperature reached after the temperature shift may be in the range of between about 30 to about 37° C., or between about 32 to about 34° C., or alternatively between about 30 to about 32° C.

The timing of the temperature shift is important to maximize productivity. If the temperature shift is performed too early, a high cell density will not be reached, or will take a long time to be reached. If the temperature shift is performed too late, it may not effectively prevent a decline in viable cell density. Preferably the timing of the temperature shift is defined in days after inoculation of the bioreactor used for the large scale production of the recombinant polypeptides. In another embodiment of the invention the timing can be defined via the cell-density that is reached in the large scale production bioreactor. For instance, the temperature shift is initiated during the linear or logarithmic growth phase of the cells or when 40 to 90% of the maximal cell density is reached. A cell density dependant set point may be expressed in relative terms (% of maximal cell density that can be reached) or absolute terms (viable cells/ml). In one specific example the cell density is chosen to be between 80 to 90%.

The timing between inoculation of the bioreactor/growth vessel and the temperature shift may range between about 3 and about 14 days depending on the specific bioreactor/growth vessel and the cell line used. Alternatively, the shift occurs between days 3 to 8. As an alternative to a single criterion as outlined above, also a dual criterion can be set by combining two of the above mentioned variables, such that selected conditions concerning time and/or cell density must be met.

If necessary for optimal growth and production, also more than one temperature step, e.g. at least 2 steps can be used, each consisting of a temperature change of at least about 1° C., alternatively at least about 2° C., where each temperature is maintained for at least one day. Thus, temperatures may be even further reduced and a more complex temperature profile can be followed.

According to the invention, the cells are grown at a first pH value before the pH shift for at least 2 days, alternatively for at least 3 days, e.g. for at least 4 days or even for at least 5 days. The pH for the first few days after starting culturing is chosen to be favourable for rapid expansion of the cell density in the bioreactor. During this time the pH of the bioreactor is controlled at a certain set point that is optimal for cell growth. Once a certain cell density is reached, it is advantageous to modify the pH of the culture. The pH is shifted after this first period of time to a second pH value which is between about 0.05-1 pH units lower than the first pH. The cells are grown at said second pH for at least 2 days. In some embodiments of the present invention the second pH value may be about 0.15 to about 1 pH units lower than the first pH. This shift in pH is usually reached by changing the pH setpoint of the bioreactor/culture vessel. The second pH value is selected to reduce cell death (e.g apotosis) and to allow maintaining high cell-specific production rates of polypeptides of adequate quality. As a consequence, in a first embodiment the timing of the pH shift is defined in days after inoculation of the bioreactor which is used for the large scale production of the recombinant polypeptide. In a second embodiment, the timing can be defined via the cell-density that is reached in the large scale bioreactor. According to a further alternative, the timing may also be made dependant on specific metabolic parameters that are measured during culturing in the cell culture medium. In one not limiting example this may be the lactate concentration. Also non-direct parameters that reflect the metabolic state of the culture can be used, such as e.g. the required dosing of $CO_2$ or controlling acid per time for maintaining the pH at the upper pH setpoint, or required dosing of NaOH or controlling caustic agent to keep the pH at a lower pH setpoint. Instead of using only one criterion for the pH shift, alternatively, a combined criterion can be set by combining parameters such as e.g. days after inoculation and cell-density.

The benefits of the pH shift strategy also involve the fact that dissolved carbon dioxide levels and addition of base can be reduced during the course of culturing, which hence avoids their negative effects. At the beginning of culturing, it is of advantage to have a higher pH value (e.g. 7.0) in the culture vessel or bioreactor, since a lower pH value (e.g. 6.8) would require higher levels of carbon dioxide in order to maintain the pH. These high levels of carbon dioxide, however can have negative effects on the cells and reduce the growth rate. In contrast, at later stages of culturing, maintaining a high pH (e.g. 7.0) requires more base addition than maintaining a low pH (e.g. 6.8). This is because lactic acid is formed and the resulting acidity must be compensated for by addition of base. The higher the pH set point, the higher the amount of base required. Base addition increases the osmolality of the culture, which can be unfavourable for growth and maintenance of a high viable cell density.

The potential benefits of the pH shift strategy can also be described from the perspective of minimizing lactic acid formation. CHO cells generally produce less lactic acid at lower pH values (e.g. 6.8) than at higher values (e.g. 7.0). Less lactic acid produced results in less base added, which is beneficial as described above.

In one embodiment the first pH is selected to be in the range between pH 6.8 and 7.5. In another embodiment the first pH is selected to be in the range between pH 6.8 and 7.2. In a further embodiment the first pH is selected to be at most pH 7, or alternatively below pH 7. The second pH value that is reached after the pH shift is in the range of between pH 6.0 and pH 7.5, or between pH 6.5 and 6.8.

The relative timing of temperature and pH shift is selected in order to achieve the most optimal result. Optimal timing of the temperature and the pH shift are chosen on a process-specific basis and made be dependent on the growth state or metabolic state of the culture. The temperature shift in principle can be implemented at a culture time point independent of the timing of the pH shift. In one embodiment of the invention the temperature shift can occur before or at the same time as the pH shift. In one embodiment of the invention the temperature shift occurs before the pH shift. For example the temperature shift may be initiated between 1-5 days before the shift in pH occurs. In another second embodiment of the invention the temperature shift is initiated at the same time as the pH shift. The term "at the same time", here refers to an ongoing shift of both respective parameters from a first value to a second value. Such simultaneous shifts may occur when the setpoint of the temperature and the setpoint of the pH have been changed and both parameters have not reached their second stable value yet. Alternatively such a scenario may occur when the setpoint in temperature was changed during the phase of a passive pH change. This occurs in case of a pH regulation by a setpoint and a deadband defining an upper and lower pH limit (see also below), in further embodiment of the invention the temperature shift may occur after the pH shift. For example the temperature shift may be initiated between 1 to 5 days after the pH shift.

In a further aspect of the present invention the pH is actively or passively changed between said first to said second pH value. There are a number of possible ways to control the pH of the cultures and to implement a pH shift In one aspect of the invention the pH is actively shifted from a first to a second pH value by changing the pH setpoint (without deadband) of the pH controller to a new value.

As a result, the change from the first pH value to the second pH value is quasi-immediate (step-change) in the culture. FIG. 1 illustrates such a step-change implementation of the pH shift, with a shift from pH 7.00 to 6.80 in this particular example. In this implementation of the invention the pH is maintained first at an upper pH value by dosing pH regulating agents accordingly (e.g. $CO_2$ or NaOH) and then changed to a lower value by actively changing the setpoint (without a deadband). The pH of the lower setpoint can be reached either by actively dosing/adding an acidifying agent to the culture resulting in a rapid change or by omitting an agent that kept the pH at the more basic first pH. Based on the size of the bioreactor and the above mentioned method of influencing the pH, the pH change may be complete within some minutes up to 24 hours.

In a further aspect of the invention the pH is allowed to passively shift (drift) from a first to a second pH value corresponding to an upper and a lower pH limit and thus to follow a cell culture specific metabolic profile. As a result, the change from the first pH value to the second pH value is gradual. This alternative way of controlling the pH of the cell culture medium and implementing a pH shift is reached by programming the pH controller of the bioreactor with a setpoint and a deadband. This defines a permissible pH range for the process, in which the pH controller takes no action. For example, a setpoint pH of 6.90 with a deadband of 0.10 pH units will define pH 7.00 as the upper pH limit and pH 6.80 as a lower pH limit. In a cell culture production bioreactor, the pH will typically be at the high limit at the beginning of the culture (first few days), where the controller prevents the pH from raising by dosing carbon dioxide into the culture. Due to the progressive accumulation of lactic acid produced by the cells, the pH will eventually decrease continuously from e.g. 7.00 to 6.80, typically within a few hours. Once the lower pH limit of e.g. 6.80 is reached, the controller prevents the pH from decreasing beyond this pH by dosing base solution into the culture. Based on the size of the bioreactor, the specific cell line, cell density or media conditions the gradual pH change may occur within a few hours or take up to a day.

In a further aspect of the invention the second pH of the culture is actively maintained after the pH shift at the second pH for the remainder of the culture time until harvest. This is accomplished by changing the pH set point to said second pH value and dosing pH regulating agents accordingly.

In a further aspect of the invention the first pH shift is followed by a second shift. The second pH shift occurs at least 1 day after the first one and the third pH value that is reached is at least 0.05 pH units higher than the second pH.

In a further aspect of the invention the second pH shift may also occur actively or passively to reach said third pH value. In the first embodiment this can be done by actively changing the pH set point as already outlined for the first pH shift (see above). The timing of the second pH shift can be defined in days after the first pH shift and/or again made dependant on metabolic parameters, such as e.g. lactate concentration. Such a shift may typically occur between 1 and 10 days after the first shift in pH. An active shift is initiated by changing the pH setpoint of the culture, pH regulating agents will be dosed accordingly.

In the second embodiment the pH can also be allowed to passively change and to follow its metabolic pH profile. This can be implemented e.g. by defining a lower and an upper pH limit as already outlined above. The upper pH limit in this case may correspond to the same upper pH limit as defined for the first pH shift or it may be altered to a new lower or a higher value. Preferably such a lower and upper pH limit may be achieved by programming the pH controller of the bioreactor with a setpoint and a deadband. Such a passive change in pH can occur by remetabolization of lactic acid late in culture by the cells, which causes the pH to increase again to values above said lower limit of the pH range. In some instances it is possible that the pH reaches again the upper limit of the range, in other cases it may also stay below that limit. The magnitude of the second pH shift may include values between 0.05 and 1 pH units. The duration of such a passive pH shift is not exactly defined since the rate of the shift/change depends on the metabolic activity and the remetabolization of lactic acid by the cells. It may typically take 0.5 to 2 days to reach the upper pH limit but in case of a passive change the pH may also remain below the defined upper threshold until the end of culturing.

Figure 2A:
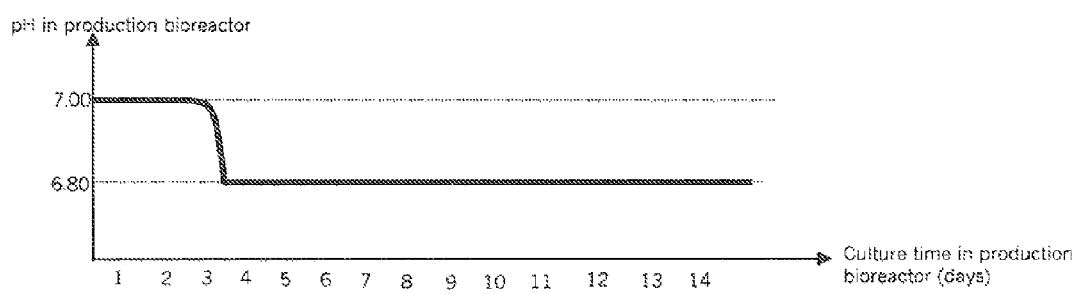
FIG. 2A shows a pH profile obtained by a passive pH shift implementation. The pH shift from 7.00 to 6.80 in the production bioreactor was reached by setting the setpoint to 6.90 and defining a deadband of 0.10. After a first pH shift to 6.80 the pH is actively maintained at 6.80 until the end of culturing.
Figure 2B:
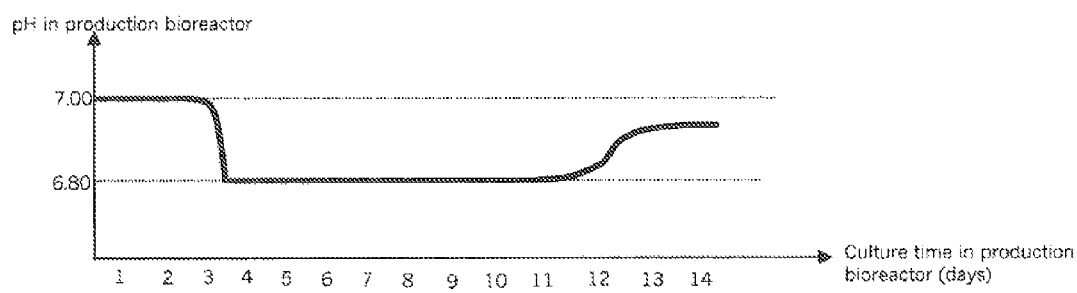
FIG. 2B shows a pH profile with a second pH shift. In this example, the upper (previous) pH limit is not reached.
Figure 2C:
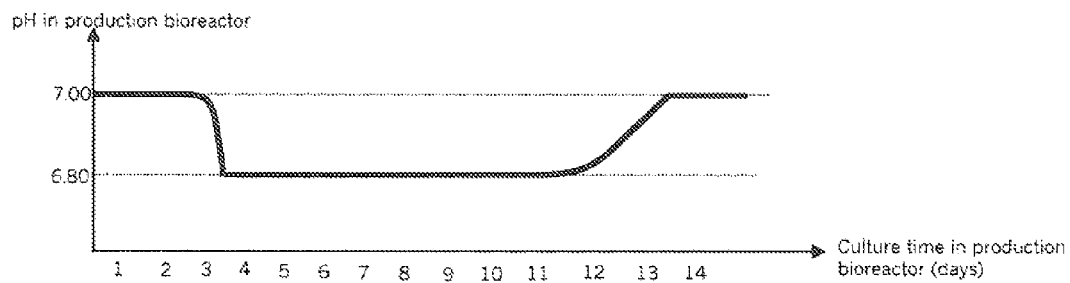
FIG. 2C shows a pH profile with a second pH shift but here the pH meets again the upper pH limit and is maintained there.

The choice of the strategy to implement will depend on multiple factors, such as sensitivity of the cells to $CO_2$ and optimal pH for product formation. Different pH profiles can be obtained by defining two or more specific set points over the course of culturing or simply by defining a setpoint and a deadband (which optionally could also be changed during culturing). Different pH profiles that can be obtained by setting a setpoint and a deadband are illustrated in FIG. 2, for a setpoint of pH 6.90 with a deadband of 0.10 as example values.

In a further aspect of the invention the total amount of the polypeptide produced by a process comprising a temperature and one or more pH shifts is greater than without combining a temperature shift with one or more shifts in pH. Combining at least one temperature shift with at least one pH shift which are adapted in terms of timing and steps size towards the needs of the particular transfected cell line has led to a much better product yield.

In a still further aspect of the invention a process comprising a temperature and one or more pH shifts has the potential to lead to a product of improved quality compared to the quality obtained without combining the temperature shift with one or more shifts in pH. One possible reason for the beneficial effect of a pH shift to lower pH values in the culture during the production phase may be the following: ammonia typically accumulates in the cell culture medium with culture time and is known to potentially affect product glycosylation, with the possible outcome of decreased product quality. Ammonia is assumed to enter the cells in the form of $NH_3$, where it can influence intracellular pH by capturing $H_3O^+$ ions. The resulting increase in intracellular pH can affect glycosylation. Shifting the pH of a culture to a lower value will decrease the concentration of extracellular $NH_3$ through an increase in protonation of $NH_3$ into $NH_4^+$, to which the cells are impermeable.

The cell culture process comprising a temperature and one or more pH shifts according to the present invention can be carried out using various cell culture media. Commonly used cell culture media that can be used are e.g., D-MEM (Dulbecco's Modified Eagle Medium), D-MEM/F-12, MEMα, Fischer's Medium, RPMI 16408ME, BGJb but is not limited to these examples. These media may be further supplemented with additional components such as e.g. nutrients, vitamins, or carbohydrates.

Suitable media that are primarily optimized for cell growth preferably contain initial amino acid concentrations according to the following ranges.

| Amino acids | Conc. (mmol/L) |
| --- | --- |
| Arginine, free base | 4.0-6.0, preferably 4.5-5.5 |
| Asparagine monohydrate | 3.0-6.0, preferably 4.0-5.5 |
| Aspartic acid | 2.5-4.0, preferably 3.0-3.6 |
| Glycine | 0.3-0.8, preferably 0.5-0.7 |
| Histidine, HCl $H_2O$ | 0.6-1.0, preferably 0.7-0.9 |
| Isoleucine | 2.0-5.0, preferably 3.0-4.0 |
| Leucine | 3.0-7.0, preferably 3.5-6.0 |
| Lysine HCl | 2.0-4.0, preferably 2.5-3.5 |
| Methionine | 1.0-1.5, preferably 1.2-1.4 |
| Phenylalanine | 1.0-2.0, preferably 1.3-1.8 |
| Proline | 2.5-6.0, preferably 3.0-5.5 |
| Serine | 3.0-8.0, preferably 4.0-7.0 |
| Threonine | 2.0-3.5, preferably 2.5-3.1 |
| Tryptophane | 0.4-1.0, preferably 0.5-0.8 |
| Valine | 2.5-5.0, preferably 3.0-4.5 |
| Tyrosine | 1.0-2.0, preferably 1.2-1.8 |
| Cystine | 0.5-1.0, preferably 0.6-0.8 |
| Glutamine | 5.5-9.5, preferably 6.2-8.2 |

Media containing amino acids as defined in the above table can be favourably used in the improved cell culture processes according to the present invention.

A further aspect of the invention includes the use of production media designed for large scale production of recombinant polypeptides. These production media may optionally contain increased amounts of components, for instance amino acids. In a preferred embodiment of the invention an initial amino acid content is used in these media in a range of between about 40 mM and about 100 mM, alternatively between about 50 and about 100 mmol/L. In an alternative embodiment of the invention such production media contain initial amino acid concentrations according to the following ranges.

| Amino acids | Conc. (mmol/L) |
| --- | --- |
| Arginine, free base | 4.0-6.0, preferably 4.5-5.5 |
| Asparagine monohydrate | 9.0-11.0, preferably 9.5-10.5 |
| Aspartic acid | 2.5-4.0, preferably 3.0-3.6 |
| Glycine | 0.3-0.8, preferably 0.5-0.7 |
| Histidine, HCl $H_2O$ | 1.0-1.5, preferably 1.1-1.3 |
| Isoleucine | 5.5-7.0, preferably 6.0-6.8 |
| Leucine | 8.0-10.0, preferably 9-9.2 |
| Lysine HCl | 3.0-6.0, preferably 4.0-5.0 |
| Methionine | 1.5-2.5, preferably 1.5-2.0 |
| Phenylalanine | 2.0-3.5, preferably 2.5-3.0 |
| Proline | 7.5-9.0, preferably 8.0-8.5 |
| Serine | 10.5-13.0, preferably 11.0-11.9 |
| Threonine | 3.5-5.5, preferably 4.0-5.0 |
| Tryptophane | 0.9-2.0 preferably 1.0-1.4 |
| Valine | 5.5-7.5, preferably 6.0-6.8 |
| Tyrosine | 1.0-3.0, preferably 2.0-2.5 |
| Cystine | 0.5-2.0, preferably 1.0-1.3 |
| Glutamine | 5.5-9.5, preferably 6.2-8.2 |
| Glutamic acid | 0.5-2.5, preferably 1.0-1.2 |

Production media containing amino acids as defined in the above table can be favourably used in the improved cell culture processes according to the present invention.

Cultivation of cells can be carried out in adherent culture, for instance in monolayer culture or preferably in suspension culture.

Large scale cultivation of cells can be used for instance by the various fermentation processes established in industrial biotechnology. Continuous and discontinuous cell culture processes can be utilized using the cell culture media according to the present invention. Other known reactor technologies, e.g. perfusion technologies or the like can be also utilized. Batch processes are one preferred embodiment.

The batch cell culture includes fed-batch culture or simple batch culture. Fed batch cell culture refers to cell culture wherein mammalian cells and cell culture medium are supplied to the culturing vessel initially and additional culture nutrients are fed continuously or in discrete increments to the culture during the culturing process with or without periodic cell and/or product harvest before termination of the culture. Simple batch culture relates to a procedure in which all components for cell culturing including the mammalian cells and the cell culture medium are supplied to the culturing vessel at the start of the culturing process.

In a further aspect of the invention, feeding of the culture is done in a fed batch process, with the feed consisting of two nutrient solutions that are added to the culture. Both nutrient solutions are added to the culture vessel either based on a predetermined schedule determined for the particular cell line and product or according to the metabolic needs which are determined by measuring the consumption of e.g. glucose or amino acids in the culture vessel. Both nutrient solutions may be added independently either as a bolus feed or continuously. Typically nutrient feed solutions comprise amino acids, at least one carbohydrate as an energy source, trace elements, vitamins or specific ions. It is particularly advantageous to use concentrated feed solutions in order to avoid large volume increase and dilution of the product. In some embodiments it may also be useful to have at least two different feed solutions. This allows independent dosing of two or more different groups of nutrients and components to the cells and thus a better adjustment of the feeding conditions concerning optimal supply of certain nutrients.

In a further embodiment of the invention, one of the two feed solutions added to the cell culture medium is a concentrated feed comprising the dipeptide cystine and the amino acid tyrosine at respective concentrations in the range of about 6.5 g/l and about 8.0 g/l and in the range of about 9 g/l and about 11 g/l in an aqueous solution at a basic pH of above 10. In a particularly embodiment, the concentrated feed comprises the dipeptide cystine and the amino acid tyrosine at respective concentrations of 10.06 g/l L-tyrosine and 7.25 g/l cystine at a pH of above 10.

The feed medium comprising cystine and tyrosine as described above can be added either based on the measured consumption of the respective amino acids or according to a fixed schedule at e.g. about 0.2 to about 0.8 wt % of the initial cell culture medium weight per day, or at about 0.4 wt % of the initial cell culture medium weight per day.

In some examples the other feed solution contains all other amino acids that are also present in the basic medium except tyrosine and cystine. In some examples this additional feed solution may consist of particular selected components such as e.g. amino acids or carbohydrates. In a further embodiment of the invention this concentrated feed medium preferably contains selected amino acids according to the following concentration ranges.

| Amino acids | Feed Medium Conc. (mmol/L) |
|---|---|
| Arginine, free base | 12.0-17, preferably 13.5-16.0 |
| Histidine, HCl H2O | 5.5-7.5, preferably 5.9-7.0 |
| Isoleucine | 21-28.0, preferably 22.0-27 |
| Leucine | 32-42, preferably 34.5-40.0 |
| Lysine HCl | 17.0-22.0, preferably 17.5-21.5 |
| Methionine | 5.5-8.0, preferably 6.0-7.5 |
| Phenylalanine | 8.5-12.0, preferably 9.0-10.5 |
| Proline | 18.0-24, preferably 18.5-22.0 |
| Serine | 39.0-49.0, preferably 39.5-46.5 |
| Threonine | 14.5-19.0, preferably 15.0-18.5 |
| Tryptophane | 3.0-5.0, preferably 3.5-4.9 |
| Valine | 23.0-29.0, preferably 23.8-27.5 |
| Glutamine | 175.0-220.0, preferably 176.0-201 |

Preferably also carbohydrates such as glucose are added to this concentrated feed medium, preferred concentrations being between about 1200 and about 1400 mmol/l, or alternatively between about 1300 and about 1395 mmol/l.

The feed medium as just described, preferably including a carbohydrate, such as glucose, can be added either based on the measured consumption of the respective amino acids or according to a fixed schedule at e.g. about 1 to about 4 wt % of the initial cell culture medium weight per day, e.g. at about 2 wt % of the initial cell culture medium weight per day.

The polypeptides that can be produced from the cell cultures and the cell culture media according to the present invention are not limited. The polypeptides can be recombinant or not recombinant. The polypeptide may be homologous to the host cell, or preferably, may be of exogenous origin. The term polypeptide as used herein encompasses molecules composed of a chain of more than two amino acids joined by peptide bonds; molecules containing two or more such chains; molecules comprising one or more such chains being additionally modified, e.g. by glycosylation. The term polypeptide is intended to encompass proteins. The polypeptide of interest may be of any origin. Preferred polypeptides of interest are of human origin, and more preferably, the proteins of interest are therapeutic proteins.

The preferred class of polypeptides produced by cell cultures and the cell culture media according to the present invention are recombinant antibodies.

The term "antibody" is used in the broadest sense and specifically covers monoclonal antibodies (including full length monoclonal antibodies), polyclonal antibodies, multispecific antibodies (e.g., bispecific antibodies), nanobodies modified antibodies, subunits of antibodies, antibody derivatives, artificial antibodies, combinations of antibodies with proteins and antibody fragments sufficiently long to display the desired biological activity. The monoclonal antibodies as used herein may be human antibodies.

However, polypeptides other than antibodies can also be produced using cell cultures and the cell culture media according to the present invention, e.g. polypeptides like transmembrane proteins, receptors, hormones, growth factors, proteases, clotting and anti-clotting proteins, inhibitor proteins, interleukins, transport factors, fusion proteins and the like.

The products obtained from such cell culture processes can be used for the preparation of pharmaceutical preparations. In addition, the protein(s) according to the invention can be administered together with other components of biologically active agents such as pharmaceutically acceptable surfactants, recipients, carriers, diluents and vehicles.

The invention is further illustrated by the following examples.

EXAMPLES

In, the Examples described below, chemically defined cell culture media 1 and 2 having the composition as detailed in the following Table 1 are used. The individual components of these cell culture media are available from standard commercial sources.

TABLE 1

| Components | Medium 1 Final conc. (mg/l) | Medium 2 Final conc. (mg/l) |
|---|---|---|
| $CaCl_2$, anhydr. | 131 | 133.2 |
| KCl, anhydr. | 800 | 800 |
| $MgCl_2$, anhydr. | 155 | 250.4 |
| NaCl | 850.6 | 500 |
| Di-Sodium hydrogenphosphate, anhydr. | 710 | 1065 |
| Sodium hydrogen carbonate, anhydr. | 2500 | 2000 |
| L-Arginine, free base | 871 | 871 |
| L-Asparagine, $H_2O$ | 616 | 1501 |
| L-Aspartic acid | 461 | 461 |
| L-Cystine | 200.1 | 304.5 |
| L-Glutamic acid Na salt Hydrate | — | 182 |
| L-Glutamic acid | — | — |
| L-Histidine, HCl—$H_2O$ | 168 | 268 |
| L-Isoleucine | 394 | 894 |
| L-Leucine | 499 | 1199 |
| L-Lysine, HCl | 621 | 821 |
| L-Methionine | 179 | 279 |
| L-Phenylalanine | 264 | 464 |
| L-Proline | 368 | 968 |
| L-Serine | 432 | 1232 |
| L-Threonin | 333 | 533 |
| L-Tryptophan | 102 | 252 |
| L-Valine | 375 | 775 |
| L-Tyrosine | 277.7 | 422.5 |
| Glycine | 38 | 38 |
| L-Glutamine | 1169.2 | 1169.2 |
| Biotin | 0.4 | 0.4 |
| D-Ca-Pantothenate | 4 | 4 |
| Folic acid | 5 | 5 |
| myo-Inositol | 40 | 140 |
| Nicotinamide | 4 | 4 |
| Pyridoxine, HCl | 2 | 2 |
| Riboflavin | 0.4 | 0.4 |
| Vitamine B12 | 2 | 2 |
| Thiamine, HCl | 4 | 4 |
| Putrescine, 2HCl | 10 | 110 |
| Cholin chloride | 40 | 240 |
| Sodium selenit ($Na_2SeO_3$) | 0.03 | 0.03 |
| Manganese chloride tetrahydrate | 0.3 | 0.3 |
| Ammonium molybdate tetrahydrate | 0.3 | 0.3 |
| Zinc chlorid, anhydr. | 3 | 3 |
| Cupric chloride dihydrate | 0.3 | 0.3 |
| Cobalt chloride hexahydrate | 0.3 | 0.3 |
| Ethanolamine | 10 | 100 |
| Monothioglycerol | 2 | — |

TABLE 1-continued

| Components | Medium 1 Final conc. (mg/l) | Medium 2 Final conc. (mg/l) |
|---|---|---|
| HEPES, acid form | 17870 | 4766 |
| Tri-Sodiumcitrate dihydrate | 911.7 | 1235.2 |
| $FeCl_3 \times 6H_2O$ | 54.1 | 4.1 |
| Pluronic F68 | 1000 | 1000 |
| D-Glucose, anhydr. | 10000 | 10000 |
| HCl | — | 327.6 |
| NaOH | 799.2 | 339.9 |

Table 2 below shows the composition of a concentrated feed medium containing L-tyrosine and cystine. The feed medium can be added either based on the measured consumption of the respective amino acids or according to a fixed schedule at e.g. 0.4% wt per day.

TABLE 2

| Components | Feed Medium (g/l) |
|---|---|
| NaOH 32% | 18.7 mL |
| L-Tyrosine | 10.06 |
| Cystine | 7.25 |

Table 3 below shows the composition of an exemplary concentrated feed medium. The feed medium can be added either based on the measured consumption of amino acids or according to a fixed schedule at e.g. 2% wt per day.

TABLE 3

| Components | Feed Medium (g/l) |
|---|---|
| L-Arginine, free base | 2.72 |
| L-Histidine, HCl—H$_2$O | 1.44 |
| L-Isoleucine | 3.44 |
| L-Leucine | 5.20 |
| L-Lysine, HCl | 3.72 |
| L-Methionine | 1.08 |
| L-Phenylalanine | 1.72 |
| L-Proline | 2.44 |
| L-Serine | 4.76 |
| L-Threonin | 2.08 |
| L-Tryptophan | 0.88 |
| L-Valine | 3.16 |
| L-Glutamine | 29.23 |
| D-Glucose-monohydrate | 275.00 |
| 25% HCL | 8.25 ml |
| 32% NaOH | 5.6 ml |

For the experiments of the examples a parental CHO cell line is used which is derived from the dhfr (+) CHO-K1 cell line ATCC CCL-61 (Kao et. al., Genetics, 1967, 55, 513-524; Kao et. al., PNAS, 1968, 60, 1275-1281; Puck et. al., J. Exp. !Vied., 1958, 108, 945-959) by adaptation to serum-free, protein-free media conditions. Three aliquots of this parental cell line are transfected to express three different monoclonal antibodies mAB1, mAB2, mAB3, respectively.

Example 1

In Example 1 two shake flask cultures containing medium 1 are inoculated in parallel with a mAb1-producing CHO clone. The shake flask cultures are incubated in a carbon dioxide incubator at 37° C. On day 3, one shake flask is transferred to a carbon dioxide incubator set at 33° C. Both shake flasks are similarly fed with two feed solutions. Feed was supplemented according to a fixed schedule, with addition of 0.4% of the first feed solution (Table 2) and 2% of the second feed (Table 3) per day starting on day 5 and lasting until the end of the culture.

Figure 3:
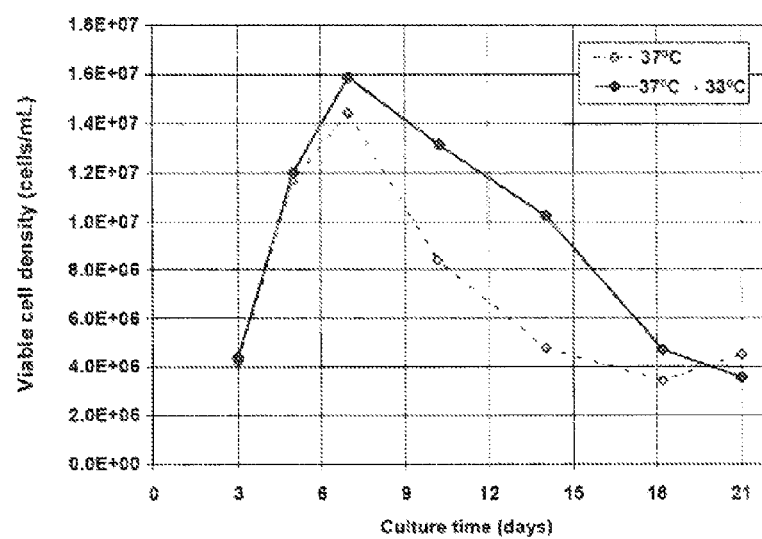
FIG. 3 shows the effect of a constant temperature versus a temperature shift on the viable cell density of a mAb1-producing CHO cell clone as function of culture time in shake flask cultures (see Example 1).
Figure 4:
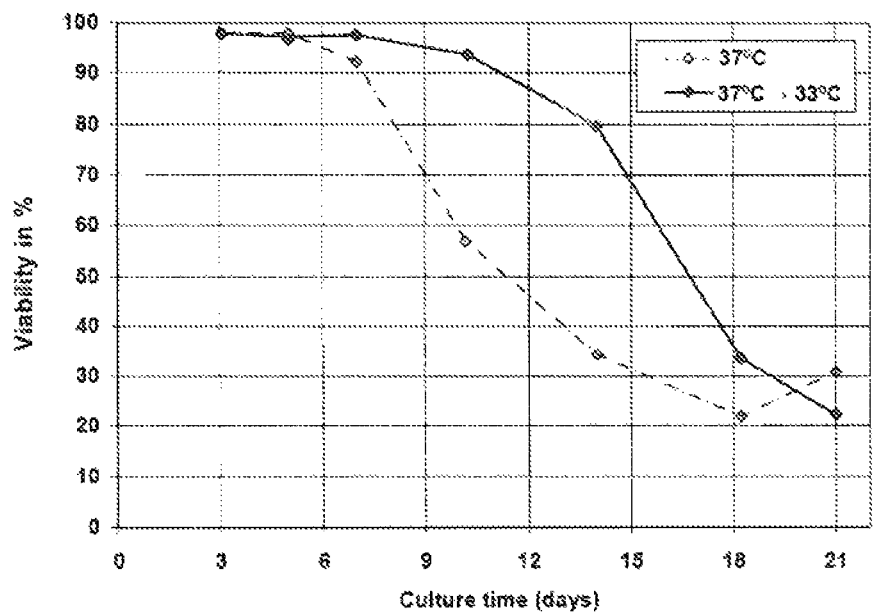
FIG. 4 shows the effect of a constant temperature versus a temperature shift on the viability of a mAb1-producing CHO cell clone (see Example 1).
Figure 5:
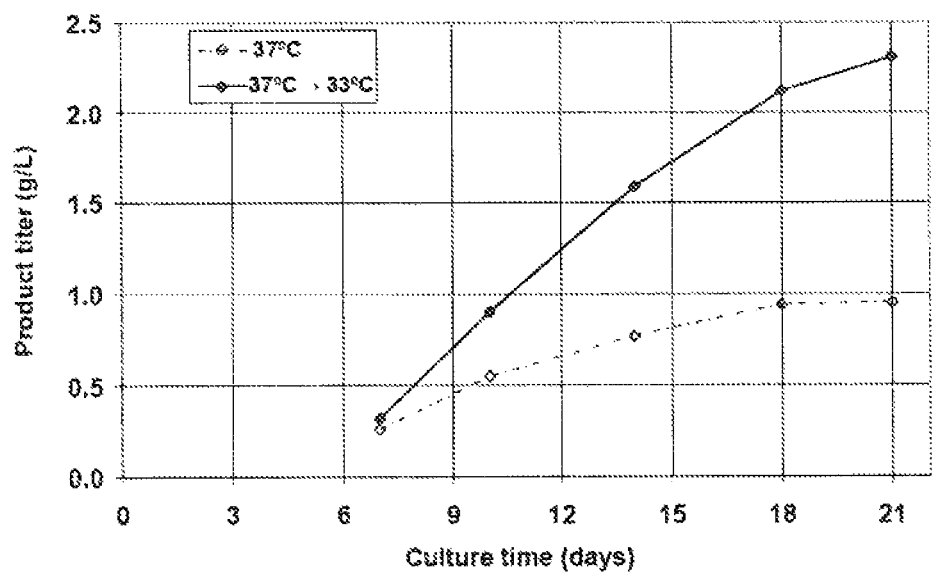
FIG. 5 shows the product titer as function of cultivation time for shake flask cultures of a mAb1-producing the CHO cell clone with and without a temperature shift (see Example 1).

The temperature shift to 33° C. enables longer maintenance of the viable cell density and viability of the culture with time (FIGS. 3 and 4) and the achievement of a higher product titer (FIG. 5), compared to the culture that is maintained at 37° C. for the whole duration of the experiment. This example illustrates the benefit of implementing a temperature shift to 33° C. during a cell culture production process based on a CHO host cell line.

Example 2

Figure 6:
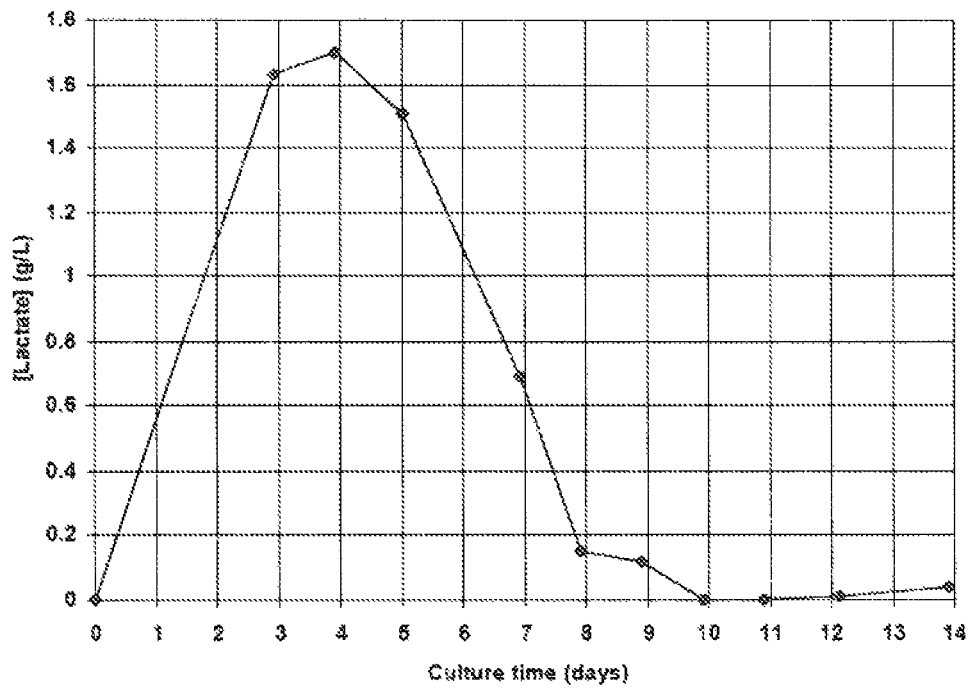
FIG. 6 shows the lactate concentration over cultivation time in a mAb2-producing clone (see Example 2).
Figure 7:
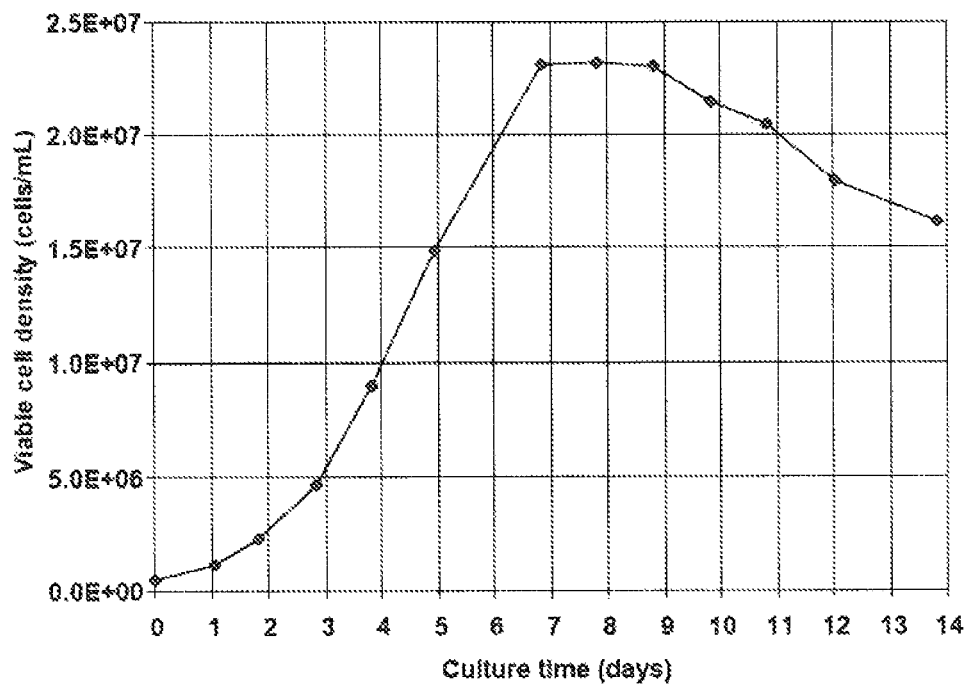
FIG. 7 shows the viable cell density as a function of cultivation time in a 300-L bioreactor with a CHO cell clone. Culture conditions included a temperature step (day 5) and two pH shifts due to pH regulation with a setpoint and a deadband (also see Example 2).
Figure 8:
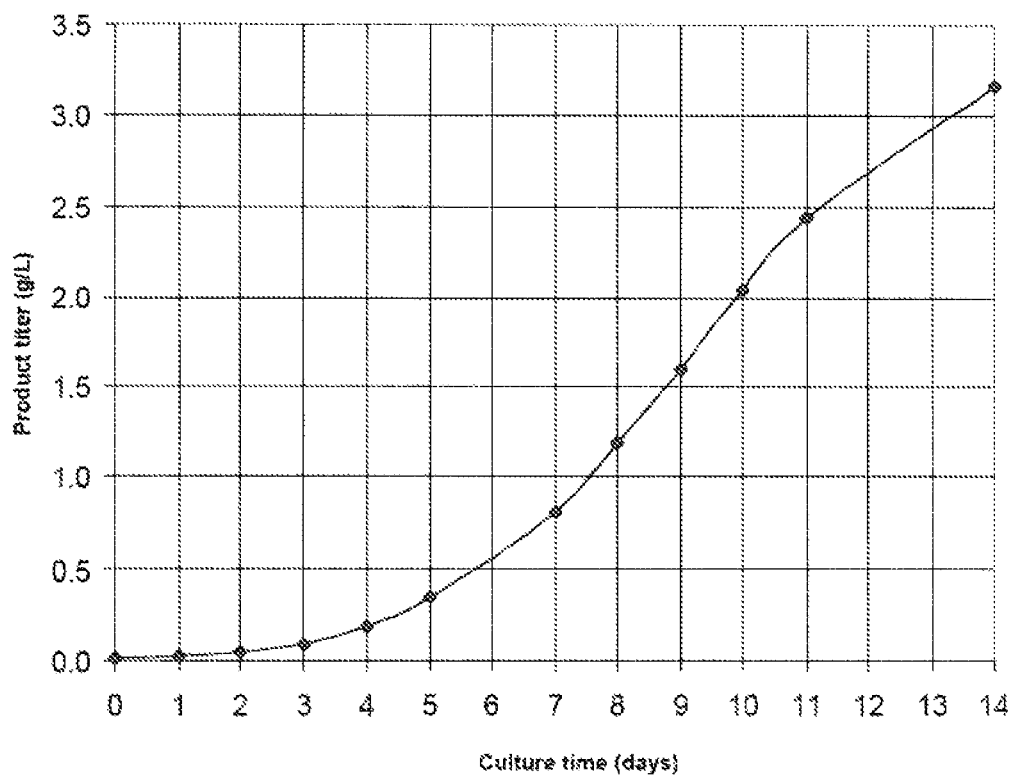
FIG. 8 shows the product titer as function of cultivation time in a 300-L bioreactor with a CHO cell clone. The process combined a temperature with pH shifts (see also FIG. 7 and Example 2).

In this example, a 300-L bioreactor containing medium 2 is inoculated with a mAb2-producing CHO clone. On day 5, the temperature of the bioreactor is shifted from 36.5° C. to 33° C. The pH setpoint is 6.90 and the deadband is 0.10. As a result, the culture starts at pH 7.00, the pH drifts down to 6.80 between day 2 and day 4, and then progressively returns to 7.00 due to lactic acid consumption by the cells (FIG. 6). The shift to pH 6.80 enables to reduce the addition of base compared to a scenario with a constant pH 7.00. The return to pH 7.00 enables to reduce the concentration of $CO_2$ in the medium compared to a scenario where the pH is left at 6.80 after the first shift. In this process that combines temperature and pH shifts, a high viable cell density is reached and the decrease in viable cell density over time is minimized (FIG. 7), allowing to reach on day 14 a high titer (FIG. 8) of product of adequate quality. Feeding is applied similarly as in Example 1.

Figure 9:
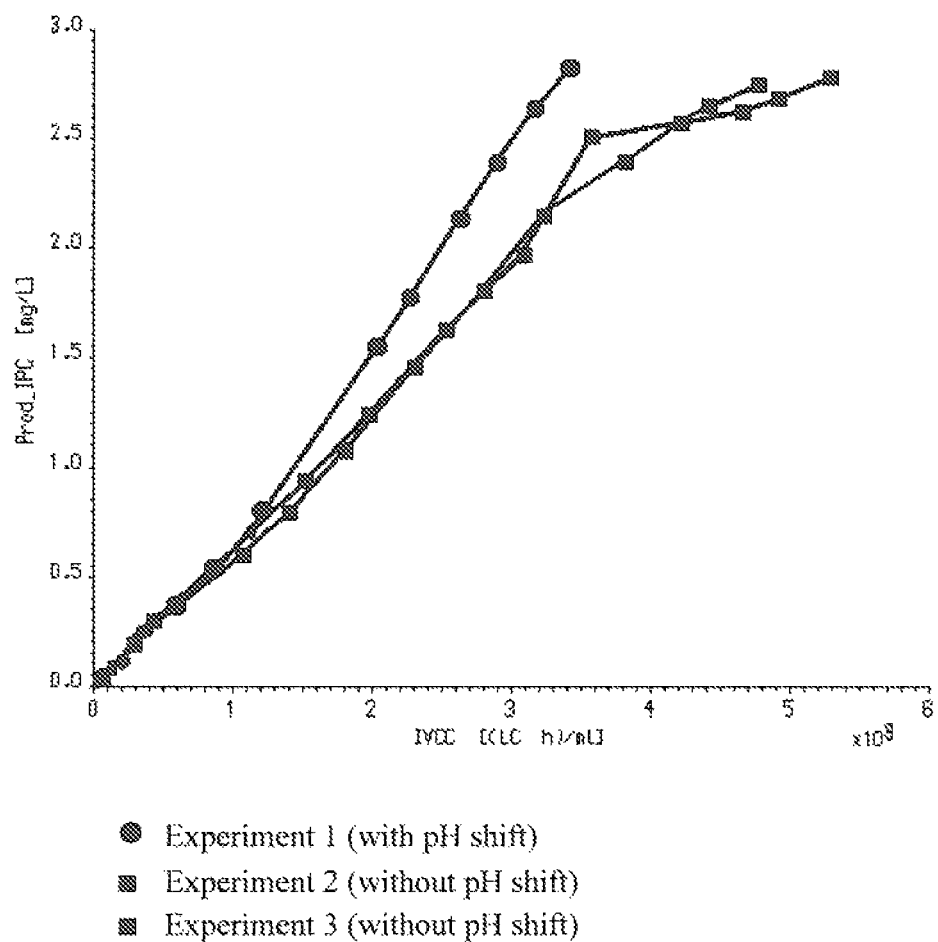
FIG. 9 shows for three independent experiments the mAb3 concentration obtained by a fed-batch process with CHO cell cultures cultivated in a glass bioreactor as a function of the integral of viable cells. Culture conditions included an identical temperature shift for all three experiments and an additional pH shift in one experiment only.

Example 3 in this example, three independent fed-batch cultivation processes are carried out in a glass bioreactor using a mAb3-producing CHO cell clone and medium 2 (see Table 1). The feed scheme of Example 1 is applied again. Two independent cultivations include a temperature shift without an additional pH shift, i.e. the pH in both cell cultures is maintained at a value of pH 7.0 over the whole length of the cultivation. The third cultivation experiment differs from the first two experiments by an additional pH shift from pH 7.0 to pH 6.8 applied at day 3 of cultivation. The temperature shift carried out in all three experiments occurred at a cell density of $4-6 \times 10^6$ viable cells/ml, respectively. In FIG. 9, the mAb3 concentration obtained as the expression product from the corresponding CHO clone is depicted as a function of the integral of viable cells (IVC) which is an integral of all living cells calculated from the cell concentration/ml VCD in a millilitre cell culture. The inclination y/x is the cell-specific productivity qp [pg/VC/h] which indicates the amount of recombinant mAb3 product a single living cell can produce in one hour. In consequence, FIG. 9 illustrates an increase of cell-specific productivity in a cell culture when subjected to an additional pH shift. Due to the additional pH shift the cells grow slower but show increased productivity.

The invention claimed is:

1. A process for the production of a recombinant polypeptide comprising culturing CHO cells in a medium under conditions comprising at least one temperature shift and at least one pH shift and expressing the recombinant polypeptide, wherein the cells are grown at a first temperature for at least 3 days after inoculation of the bioreactor and the temperature is then shifted to a second temperature which is between about 1 and about 8° C. lower than the first temperature and the cells are maintained at said second temperature for a period of at least another 2 days;

the cells are grown at a first pH value for at least 2 days after inoculation of the bioreactor and the pH is then shifted to a second pH value which is between about 0.05 and about 1 pH units lower than the first pH and the cells are grown at said second pH for at least 1 day.

2. The process according to claim 1 wherein the pH is actively changed between said first and said second pH value.

3. The process according to claim 1 wherein the pH is passively changed between said first and said second pH value.

4. The process according to claim 1 wherein the first temperature is in the range of between about 33° C. and about 38° C.

5. The process according to claim 1 wherein the second temperature is in the range of between about 30° C. and about 37° C.

6. The process according to claim 1 wherein the first pH value is in the range of between about pH 6.8 and about pH 7.5.

7. The process according to claim 1 wherein the second pH value is in the range of between about pH 6.0 and about pH 7.1.

8. The process according to claim 1 wherein said second pH is actively maintained until the end of culturing.

9. The process according to claim 1 wherein the first pH shift is followed by a second pH shift after at least 1 day with the third pH value being about 0.05 pH units to about 1 pH unit higher than the second pH value.

10. The process according to claim 9 wherein the pH is actively changed from said second to said third pH value.

11. The process according to claim 9 wherein the pH is passively changed from said second to said third pH value.

12. A process for the production of a recombinant polypeptide comprising culturing CHO cells in a medium under conditions comprising at least one temperature shift and at least one pH shift and expressing the recombinant polypeptide, wherein the cells are grown at a first temperature for at least 3 days after inoculation of the bioreactor and the temperature is then shifted to a second temperature which is between about 1 and about 8° C. lower than the first temperature and the cells are maintained at said second temperature for a period of at least another 2 days;

the cells are grown at a first pH value for at least 2 days after inoculation of the bioreactor and the pH is then shifted to a second PH value which is between about 0.05 and about 1 pH units lower than the first pH and the cells are grown at said second pH for at least 1 day, further wherein the medium is protein- and serum-free and characterized by a total amino acid content of between about 40 and about 100 mM.

13. The process according to claim 1 wherein culturing is done in fed batch mode comprising feeding of at least two nutrient solutions that are added to the culture.

14. The process according to claim 13 wherein one of the feed solutions added to the culture medium is a feed comprising the dipeptide cystine and the amino acid tyrosine.

15. The process according to claim 14 wherein the feed comprises the dipeptide cystine and the amino acid tyrosine at respective concentrations in the range of about 6.5 g/l and about 8.0 g/l and in the range of about 9 g/l and about 11 g/l in an aqueous solution at a basic pH of above 10.

16. The process according to claim 14 wherein the amount of the feed solution comprising cystine and tyrosine is added to the culture medium in the range of about 0.2 and about 0.8 wt % of the initial culture medium weight per day.

17. The process according to claim 1 wherein the produced polypeptide is glycosylated.

18. The process according to claim 1, wherein the polypeptide is an antibody or antibody fragment.

* * * * *